(12) United States Patent
Levinson

(10) Patent No.: US 7,435,242 B2
(45) Date of Patent: Oct. 14, 2008

(54) URINATION APPARATUS

(76) Inventor: Orde Levinson, Caudwell's Castle, Folly Bridge, Oxford OX1 4LB (GB)

( * ) Notice: Subject to any disclaimer, the term of this patent is extended or adjusted under 35 U.S.C. 154(b) by 806 days.

(21) Appl. No.: 10/239,901

(22) PCT Filed: Mar. 29, 2001

(86) PCT No.: PCT/GB01/01413

§ 371 (c)(1), (2), (4) Date: Feb. 6, 2003

(87) PCT Pub. No.: WO01/74275

PCT Pub. Date: Oct. 11, 2001

(65) Prior Publication Data

US 2003/0149408 A1    Aug. 7, 2003

(30) Foreign Application Priority Data

| Mar. 30, 2000 | (GB) | ................................ | 0007773.5 |
| Jul. 28, 2000 | (GB) | ................................ | 0018669.2 |
| Jan. 24, 2001 | (GB) | ................................ | 0101871.2 |
| Feb. 19, 2001 | (GB) | ................................ | 0104046.8 |

(51) Int. Cl.
A61F 5/44 (2006.01)
A47K 11/00 (2006.01)

(52) U.S. Cl. ....................... 604/329; 604/330; 604/346; 604/347; 604/355; 4/144.1; 4/144.2; 4/144.3; 4/144.4

(58) Field of Classification Search ......... 604/329–331, 604/346, 347, 355; 4/144.1, 144.2, 144.3, 4/144.4, 454, 462; D24/122; 119/869; 600/574
See application file for complete search history.

(56) References Cited

U.S. PATENT DOCUMENTS 190,244 A * 5/1877 Olmstead ..................... 4/144.1

(Continued)

FOREIGN PATENT DOCUMENTS

EP    0 464 575 A1    1/1992

(Continued)

OTHER PUBLICATIONS

Product Reference Card, Beambridge Medical, Surrey, UK.

(Continued)

*Primary Examiner*—T. Zalukaeva
*Assistant Examiner*—Michael G Bogart
(74) *Attorney, Agent, or Firm*—Lawrence E. Laubscher, Jr.

(57) ABSTRACT

The present invention relates to urination apparatus for urine sample collection for testing of urine, waste urine collection for disposal of urine resulting from urination away from toilets, and simplification of urination by women without sitting on a toilet. A urine sample collection apparatus (100B) has a tubular portion (3) having a coupling (60A) in the side thereof formed for releasably mounting an open topped urine sample collection container (70) thereto in a direction extending generally away from the axis of said tubular portion. The apparatus also has a urine receiving receptor (1B) with a surface portion (4B) extending from a rim (5B), bounding an inlet surface which is symmetrical about the axis of said tubular portion, to an aperture (2B) from which said tubular portion extends in a direction generally away from said inlet surface. The edge of the rim (110'B) on the side corresponding to said coupling is displaced along the axis of the tubular portion further from the aperture than the opposing edge of the rim (110'A).

14 Claims, 6 Drawing Sheets

U.S. PATENT DOCUMENTS

| | | | | |
|---|---|---|---|---|
| 1,951,871 A * | 3/1934 | Judah | | 4/114.1 |
| 3,473,172 A * | 10/1969 | Friedman et al. | | 4/144.3 |
| 3,485,233 A * | 12/1969 | Cord | | 600/574 |
| 3,750,647 A | 8/1973 | Gleason et al. | | |
| 4,202,058 A * | 5/1980 | Anderson | | 4/144.3 |
| 4,494,581 A | 1/1985 | Gordon | | |
| 4,568,339 A * | 2/1986 | Steer | | 604/329 |
| 4,771,484 A * | 9/1988 | Mozell | | 4/144.4 |
| 4,815,151 A | 3/1989 | Ball | | |
| 4,911,698 A * | 3/1990 | Wapner | | 604/329 |
| 4,936,838 A * | 6/1990 | Cross et al. | | 604/329 |
| 4,986,823 A * | 1/1991 | Anderson et al. | | 604/329 |
| 5,091,998 A * | 3/1992 | Witzke | | 4/144.4 |
| 5,147,301 A * | 9/1992 | Ruvio | | 604/97.02 |
| 5,408,703 A * | 4/1995 | Cicio | | 4/144.2 |
| 5,457,823 A * | 10/1995 | Mojena | | 4/144.2 |
| 5,571,095 A * | 11/1996 | Lu | | 604/329 |
| 5,742,948 A * | 4/1998 | Cicio | | 4/144.3 |
| 5,842,233 A * | 12/1998 | Broden | | 4/144.1 |
| 5,893,176 A * | 4/1999 | Magiera et al. | | 4/144.4 |
| 5,894,608 A * | 4/1999 | Birbara | | 4/144.3 |
| 5,920,916 A * | 7/1999 | Norton | | 4/144.3 |
| 5,956,782 A * | 9/1999 | Olguin | | 4/454 |
| 5,957,904 A * | 9/1999 | Holland | | 604/331 |
| 6,021,530 A * | 2/2000 | Davis | | 4/144.3 |
| 6,123,691 A * | 9/2000 | Karavani et al. | | 604/329 |
| 6,183,454 B1 * | 2/2001 | Levine et al. | | 604/329 |
| 6,202,225 B1 * | 3/2001 | Beck et al. | | 4/144.2 |
| 6,299,606 B1 * | 10/2001 | Young | | 604/329 |
| 6,394,988 B1 * | 5/2002 | Hashimoto | | 604/355 |
| 6,398,742 B1 * | 6/2002 | Kim | | 600/574 |
| 6,460,200 B1 * | 10/2002 | Mottale et al. | | 4/144.4 |
| 6,547,771 B2 * | 4/2003 | Robertson et al. | | 604/317 |
| 6,592,560 B2 * | 7/2003 | Snyder | | 604/331 |
| 6,719,741 B2 * | 4/2004 | Ching | | 604/329 |
| 6,740,066 B2 * | 5/2004 | Wolff et al. | | 604/319 |
| 2002/0026161 A1 * | 2/2002 | Grundke et al. | | 604/327 |

FOREIGN PATENT DOCUMENTS

| | | | |
|---|---|---|---|
| FR | 2 590 160 | | 5/1987 |
| GB | 2 090 144 A | * | 7/1982 |
| GB | 2 092 690 A | * | 8/1982 |
| GB | 2 107 190 A | | 4/1983 |
| GB | 2 247 626 A | | 3/1992 |
| WO | WO 90/13280 | | 11/1990 |
| WO | WO 98/43563 | | 10/1998 |
| WO | WO 01/74275 | | 10/2001 |
| WO | WO 2005/089687 A2 | * | 9/2005 |

OTHER PUBLICATIONS

Portable Urinal 51150, Advertising Brochure.
URlbag and URlfem, Advertising Brochure, Manfred Sauer GmbH, Northampton, UK.
EWZ Travel Pack, Advertising Brochure.

* cited by examiner

URINATION APPARATUS

The present invention relates to urination apparatus for use in three situations: urine sample collection for testing of urine, waste urine collection for disposal of urine resulting from urination away from toilets, and simplification of urination by women without sitting on a toilet.

There are a large number of reasons why urine is sampled, usually for legal or medical reasons, and for biochemical and bacteriological testing.

With regard to the legal reasons, the police use urine analysis for drink drive testing, drug abuse, DNA testing, and also for male and female rape allegations. Competitive sports events, including military ones, routinely make such tests.

With regard to the medical reasons, the medical profession routinely use urine analysis for detection of protein, for detection of bladder infections, for detection of drugs, hormones, proteins, and pregnancy, and for any fetal or other abnormality during pregnancy or any infectious diseases which may be passed on to the unborn child. Further tests include the 10 SG tests (also know as the U10 tests) which as a single test covers the following 10 parameters: Glucose, bilirubin, ketone, specific gravity, blood, pH, protein, urobilingogen, nitrite and leukocytes.

With the increased sophistication of modern equipment these can be tested in a number of combinations known as 9SG, 4B, 3, 2K or 1G and can be done on machines that are so small that they can be accommodated in the surgeries of general practitioners. The advantages of such machinery are that the patients's results are almost instantaneous (whereas some results can take 3-14 days) and are secure (they are not confused with any other patient or lost in postage or broken in transit). Further machinery for the testing of urine includes dipsticks in test tube bottles of a wider than normal diameter, which can also realize results for any types and density of bacterial growths and for any of the denominations of the agar media. The increased sophistication of machinery (and the desire of patient's for more immediate results) has placed a greater significance on the collection of urine samples. The above are given as examples only and do not constitute an exhaustive list of the types of tests or situations in which such tests are required.

Initially, a simple container was used into which an individual would urinate, these traditional containers being known as "sweetheart pots". Either the urine in the container would be tested directly, or a sample would be pipetted out and tested then, or a small quantity of the urine sample would be transferred to a transfer bottle, typically of 20 ml, for later testing.

However, the normal voiding quantity of urine for adults is typically between 250-450 ml. Therefore, either a large sweetheart pot must be used or urine overflows the sweetheart pot. This results in either a mess on the surface or floor on which the sweetheart was resting or in spillage onto the hands of the individual holding the sweetheart pot. In the latter case, there are a number of drawbacks. Most individuals exhibit a high degree of squeamishness when it comes to urine, either through direct contact or in clearing up urine. There is also a risk of infection from contagious diseases. Thus, the above situation, as well as being unhygienic, messy and inconvenient, causes considerable distress and embarrassment to the individual giving the sample. This is particularly the case where the individual is in a sensitive state, perhaps because of a medical condition or through having been the victim of a criminal act.

One alternative is therefore to use a large capacity sweetheart pot. However, a problem with large capacity sweetheart pots arises because the sample volume actually required for most tests is much smaller than the capacity of the sweetheart pot. Accordingly, it is necessary for someone to decant some of the urine from the sweetheart pot into a smaller testing container used for the test. This transfer of urine from the sweetheart pot to the smaller testing container (and/or for transporting the sample to the location at which the test will be carried out) represents a further messy process having similar drawbacks to those mentioned above. In the event that another party performs the transfer, for example a nurse or a police officer, then they too need protection from contact with the urine sample. Moreover, due to the use of the sweetheart pot and the smaller testing container, the risk of contamination is greater.

Another alternative is to make the sweetheart pot smaller or to ask the individual to provide the sample directly into a smaller testing container. However, in this case, it is necessary to urinate into what are typically tubular or bottle shaped testing containers having a relatively small inlet surface. This makes it difficult for an individual to hold the testing container in their urine stream without contaminating their hands and the outside of the container. This is difficult enough when sitting down. However, even in surgeries and police stations, public toilets are often unhygienic because they have been Boiled in some way by previous users. Therefore, women in particular often feel that they have to adopt an uncomfortable, hovering stance over a public toilet seat, making it even more difficult to provide the required sample. Thus, this alternative has similar drawbacks to those mentioned above.

It is estimated that some 120 million urine samples are taken each year in the United Kingdom, mostly using the aforementioned smaller testing container. The size of the container employed varies according to manufacturer and geographical area. Indeed, the container also doubles up for collection of blood and the like. Thus, such containers have been used for a long time.

One apparatus specifically directed at obtaining a mid stream urine sample is disclosed in WO-A-90/13280. This document describes a urine sample collection apparatus and a waste urine collection apparatus wherein a front body contacting portion is connected to one end of an elongate tube which has a sampling passage located immediately adjacent that one end. The other end of the elongate tube can be open or joined to a disposal container. A mid stream sample container is attached to the sampling passage via a fracturable join. In use, the front portion is located against a female user's body such that the rim thereof surrounds the user's ostium and the user then discharges urine into the apparatus. By selective breakage of the fracturable join, a mid stream sample of urine passes through the sampling passage into the sample container. Alternatively, the urine can simply pass to a disposal container. The shape of the front portion is generally funnel shaped flaring uniformly from the connection to the one end of the tube out to a curved body contacting surface.

Thus, this known apparatus intends to provide a means by which the urine flow can pass out into a toilet whilst a proportion of the urine flow can be selectively collected in a sweetheart type of collection container. However, the collection container that collects the urine can not easily function as a testing container or provide a container which can be transported. Furthermore, there is still spillage of urine over the users's hands during urination; and spillage as the user attempts to separate the collection container from the apparatus. In addition, the body contacting end of the apparatus leaks and a back pressure is created that tends to contaminate the contacted area of the body with urine. There is also significant splashing of the female body that is within the area bounded by the contact of that portion with the body. It has also been found that certain of these apparatus do not fill correctly. It is believed that this is partly due to air locks being present, due to the orientation of the apparatus and collection container, and the speed and pressure of the urine flow. The apparatus can also not accommodate differing flow rates. Furthermore, this apparatus is difficult to use. The complexity of its manufacture makes it much more expensive than the aforementioned smaller sample containers. For the above reasons, this apparatus has not been commercially successful.

Other known urine sample collection apparatus have a body contacting portion which is funnel shaped and leads directly to a container. However, once again, it has been found that when such apparatus are used by a female user, the known funnel shape of the body contacting portion can result in backing up of urine within that portion, significant splashing of the female body that is within the area bounded by the contact of that portion with the body, or leakage around the rim thereof. This is unpleasant, messy, and unhygienic. It is a major inhibition to female users using such apparatus.

There is also known a leisure urination apparatus directed to the simplification of urination by women without sitting on a toilet. Such an apparatus comprises an elongate tube having one end which is partially narrowed whilst the other end is connected to open onto a front portion in the form of a relatively small shovel or scoop shaped receptor. In use, a female user places the receptor under her outer labial lips and around her urethra orifice. The outer labial lips then act as a leak-proof fit and secures the receptor in place. The user then starts to urinate. The urine flows down the tube and out through the narrowed end. Thus, the exit of urine can be preferentially directed, for example into a toilet or urinal, or against a tree or rock. In particular, the female user does not need to significantly undress to perform the act of urination. This is advantageous in many outdoor situations. Hence the term leisure urination apparatus.

However, some female users find the concept of locating this receptor under the outer labial lips distasteful and will not do it. It is a major inhibition to female users using such apparatus.

It is an object of the present invention to provide an improved body contacting portion which does not suffer the drawbacks associated with the known urination apparatus.

Another object of the invention is to provide a urine sample collection apparatus which reduces the likelihood of contamination of the individual's hands and/or a container in which the urine is collected for transport and/or testing.

Another object of the invention is to facilitate the collection of urine samples from children.

Another object of the invention is to provide an apparatus which allows bed-ridden and/or disabled people to urinate comfortably and hygienically.

A further object of the invention is to facilitate urination, at home or elsewhere, by people who (permanently or temporarily) have difficulty in adopting a comfortable position for urination, such as pregnant women, women with broken legs, the obese and so-on.

Yet another object of the invention is to relieve pressure upon carers, nurses and hospital staff by enabling bed-ridden or wheelchair bound patients to deal with some at least of their own urinary processes without the need to call for attention.

A still further object of the invention is to provide a means which renders the action of urinating by such people easier to manage without assistance, thereby improving their quality of life and self-esteem.

STATEMENTS OF INVENTION

According to one aspect of the present invention there is provided a urine sample collection apparatus comprising:
  a generally elongate tubular portion having an outlet in the side thereof including a coupling formed for releasably mounting an open topped urine sample collection container thereto in a direction extending generally away from the axis of said tubular portion; and
  a receptor for reception of urine, the receptor having a rim shaped for intimate contact with a user's body and a surface portion from which said tubular portion extends in a direction generally away from a surface bounded by said rim;
  wherein the surface portion of the receptor, the direction of said tubular portion and the direction of said urine collection container are selected whereby urine voided from the body at normal speeds and pressures flows along said tubular portion whilst filling said container.

According to a further aspect of the present invention there is provided a urine sample collection apparatus comprising:
  a generally elongate tubular portion having an outlet in the side thereof including a coupling formed for releasably mounting an open topped urine sample collection container thereto in a direction extending generally away from the axis of said tubular portion; and
  a receptor for reception of urine, the receptor having a surface portion extending from a rim, bounding an inlet surface which is symmetrical about the axis of said tubular portion, to an aperture from which said tubular portion extends in a direction generally away from said inlet surface;
  wherein the edge of the rim on the side corresponding to said outlet is displaced along the axis of the tubular portion further from said aperture than the opposing edge of said rim.

According to a still further aspect of the present invention there is provided a urine sample collection apparatus comprising:
  a generally elongate tubular portion having an outlet in the side thereof including a coupling formed for releasably mounting an open topped urine sample collection container thereto in a direction extending generally away from the axis of said tubular portion; and
  a receptor for reception of urine, the receptor having a surface portion extending from a rim, bounding an inlet surface which is symmetrical about the axis of said tubular portion, to an aperture from which said tubular portion extends in a direction generally away from said inlet surface;
  wherein the inlet surface of the receptor, the direction of said tubular portion and the direction of said urine sample collection container are selected whereby when the rim is held, during use, against the body of a female user to cover the urethra orifice, the open top of the sample urine collection container is generally horizontal or faces towards urine voided from the body.

According to yet a further aspect of the present invention there is provided a urine sample collection apparatus comprising:
  a generally elongate tubular portion having an outlet in the side thereof including a coupling formed for releasably mounting an open topped urine sample collection container thereto in a direction extending generally away from the axis of said tubular portion; and
  a receptor for reception of urine, the receptor having a surface portion extending from a rim, bounding an inlet surface which is symmetrical about the axis of said tubular portion, to an aperture from which said tubular portion extends in a direction generally away from said inlet surface;

wherein the receptor and the tubular portion are formed such that when the rim is held, during use, against the body of a female user to cover the urethra orifice, said aperture is generally opposite the urethra orifice with the tubular portion oriented downwards and generally parallel to the natural flow of urine from the woman during urination.

The user of the apparatus could be either male or female, but the apparatus is particularly applicable to female use. The apparatus of the present invention thus aids collection of urine for testing because it does not require the user to aim a stream of urine into a relatively small inlet surface of a typical urine sample collection container. In this connection, the user can hold the apparatus with the hand positioned so that the fingers are beneath the tubular portion with the thumb on top, thus permitting the apparatus to be held steady and reducing contamination of the user's hands, with the excess urine being directed to a suitable disposal site. In addition, since the urine is directed into the urine sample collection container through the coupling, the outside of the urine sample collection container itself does not become contaminated. Thus, the potentially degrading known situation of giving a urine sample is avoided. Moreover, since a urine sample can be given without contamination of the users hands, people who avoided giving urine samples because of squeamishness are more likely to give a urine sample. The ease of use and reduced risk of contamination makes it easier for assistants to help users without themselves getting contaminated. In addition, the present invention is particularly advantageous for urine sample collection from disabled and young children without contamination.

Furthermore, there is no need for the urine to be transferred to another container, since the urine sample collection container may have any desired capacity.

The apparatus of the present invention is such that it is easy to use so that users can readily understand how a sample is to be given. Accordingly, a good sample can be reliably obtained. Furthermore, the apparatus can be easily used by both sexes who are disabled, elderly, infirm, or obese since it is usable whilst sitting on a toilet or standing before a urinal. In addition, for women, this avoids the risk of contamination from toilet seats in public toilets.

Additionally, since the apparatus of the present invention has a simple form and construction, it can be made as one piece from medical grade plastics at a price level that renders it practical for Health Authorities to introduce.

The apparatus can be pointed more horizontally, for example at a urinal, or can be pointed more vertically down into a toilet bowl. In the latter respect, the compact design of the apparatus facilitates its simple usage whilst sitting on a toilet. Consequently, the apparatus can be used by both males and females either in a standing or sitting position.

Moreover, by having the inlet surface and the tubular portion arranged in this way, the urine flow is along the tubular portion so that less back pressure or back flow is likely thereby reducing the risk of contamination of the users body. In addition, a vacuum effect is produced which can suck the receptor onto the body thereby enhancing the seal between the receptor and the body. In addition, splash-back onto the body bounded by the rim is substantially reduced. This dryness during use differs noticeably from the prior art and is considered very beneficial by users.

Preferably, said inlet surface has a generally concave shape to fit the generally convex shape of the female body in the proximity of the urethra orifice.

By making the inlet surface with this shape, the apparatus has a complementary fit with the area around the urethra orifice for females in particular. Thus, a good seal at the body is provided to ensure that there is no leakage between the apparatus and the body, particularly at the high pressures that occur during urination.

It is preferred that the end of the tubular portion remote from the receptor is substantially closed excepting an excess overflow outlet.

This allows urine to flow out of the tubular portion in a direction away from the user, after the urine sample collection container is full. This urine can be directed into any suitable disposal site, such as a toilet bowl, urinal or into any suitable container or receptacle placed in fluid contact with the excess overflow outlet. For example, a bag produced from plastics material and having a suitably dimensioned, elasticated neck can be secured, by its neck, in communication with the overflow outlet. The provision of an overflow outlet is a convenient feature because generally the user will void significantly more urine than is required to fill the urine sample collection container.

In one embodiment, the receptor and the tubular portion are integrally formed.

For this reason the apparatus can be easily formed from a single mould making production cheap and easy.

In another embodiment, the receptor and the tubular portion are separately formed and mechanically connected together.

This provides the opportunity for parts of the apparatus to be sterilized for re-use.

It is preferred that the coupling is directed away from the axis of the tubular portion at a fixed angle other than a right angle.

By having the coupling directed in this way, the urine sample collecting container, which is mounted parallel to the coupling, can be arranged to be substantially vertical when the apparatus is in use by a female sitting down.

In a particularly preferred embodiment, the outlet is located along the tubular portion to be spaced from the aperture of the receptor.

By having the outlet spaced in this way, the flow of urine along the tubular portion has slowed sufficiently to enable a part of the flow to go into the urine sample collection container. In addition, the space between the outlet and the receptor provides a finger space to assist the user in holding the apparatus.

In a particular case, the outlet is spaced from the aperture of the receptor by at least 1.5 cm.

It has been found that this dimension provides a suitable position where the urine flow has slowed sufficiently and gives an appropriate dimension for the finger space.

Conveniently, the surface of the tubular portion on the side of said outlet and which is adjacent said outlet is curved away from said axis to meet the outlet.

By having this surface curved in this manner, the diversion of a proportion of the main urine flow into the urine sample collection container is assured.

In one embodiment, the outlet comprises a stub-like tubular section extending away from the tubular portion.

As a result, the section can provide a push fit connection for the urine sample collection container, although a bayonet or other connection could be used. Moreover, it is found that during separation of the urine sample collection container therefrom, substantially no spillage of urine therefrom needs to occur.

In a particular case, the stub-like section extends away from the tubular section to have a decreasing diameter to provide a friction fit to the urine sample collection container.

Consequently, the section provides a push fit connection which is compatible to differing diameter urine sample collection containers. Thus, the apparatus can be applied to a very wide range of collection containers.

It is preferred that the rim is formed whereby when the rim is held, during use, against the body of a female user to cover the urethra orifice, in a standing or sitting position, the tubular portion points in a generally downward direction.

Thus, disposal of the excess urine is facilitated.

In one preferred embodiment, the rim and surface portion of the receptor define a shovel like shape.

This particular shape has been found to be particularly good at making a seal with the female anatomy in the vicinity of the urethra orifice. In fact, it is preferred that the rim of the receptor is shaped to fit intimately over a woman's urethra orifice.

In one case, the rim defines a generally oblong shape.

This has been found to provide improved sealing to the body of the user.

In one case, the receptor is sized to fit beneath the outer labial lips of a female user during use.

This has been found to be particularly convenient since a vacuum effect is facilitated whereby the receptor tends to be sucked onto the woman to provide a very good seal. Moreover, the degree of contamination of the woman is minimised. In addition, women use the apparatus without having to take down their trousers or panties. In this connection, trousers can be unzipped or unbuttoned and panties moved to one side before engaging the receptor to cover the urethra orifice. Then, without having to sit on a toilet seat, a woman can urinate with confidence into the apparatus. Moreover, since urine has anti-septic properties, the lack of spillage can reduce the pain associated with giving a urine sample when the user has wounds, sores or lesions in or around the female genital area, has an outbreak of certain female genital infections, during the post natal period when an episiotomy has been performed etc.

In another case, the rim defines a generally key-hole shape.

This has been found to provide improved sealing to the body of the user.

In a preferred embodiment, the receptor is sized to cover the outer labial lips of a female user during use.

Thus, inhibitions with locating the receptor under the outer labial lips is avoided whilst still providing the aforementioned vacuum effect to provide a very good seal. Moreover, the degree of contamination of the woman is minimised.

According to still another aspect of the present invention there is provided a urine funnelling trumpet comprising:
  a relatively narrow outlet aperture flaring out to a bell with a rim defining an inlet area;
  wherein the inlet area has a long axis with a pubic locating portion extending from one end of the axis to meet a vaginal locating portion extending from the other end of the axis, the inlet area of the pubic locating portion being inclined relatively towards the inlet area of the vaginal locating portion.

The term "trumpet" as used herein is intended to encompass an apparatus having an aperture to which a tube can be joined, integrally or separably, and which has a flared bell which is bowl shaped.

It has been found that the relative inclination of the two portions of the urine funnelling trumpet aids in the location thereof over the region of the urethra orifice, and also enables a good seal to be provided by the rim when pushed against the body. In particular, it has been found that it is natural for the female user to locate the pubic locating portion over the pubic area and the vaginal locating portion over the vaginal lips.

In a preferred embodiment, the inlet area of the vaginal locating portion has a curvature along said axis.

This improves the seal provided by the rim of this portion when pushed against the body.

In a particular case, the vaginal locating portion is dimensioned to fit substantially closely around the vaginal lips of a female user.

This ensures a good seal to the body of a female.

In a preferred embodiment, the inlet area of the vaginal locating portion is symmetrical about said axis.

This improves the seal provided by the rim of this portion when pushed against the body.

In another embodiment, the inlet area of the pubic locating portion has a curvature along said axis.

This improves the seal provided by the rim of this portion when pushed against the body.

Conveniently, the inlet area of the pubic locating portion is symmetrical about said axis.

In one embodiment, the side of the bell flaring out from the outlet aperture meets the rim at said one end of the axis substantially as a tangent to the curvature of the inlet area of the pubic locating portion to provide a generally flat surface in the region of said one end of the axis.

This has been found to improve the seal provided by the rim of this portion when pushed against the body and facilitates a good seal even with variation in the physique of the female user.

In a preferred embodiment, the radius of curvature of the vaginal locating portion is no more than 20% smaller than the radius of curvature of the pubic locating portion.

This has been found to provide a good seal with the female body which avoids leakage and aligns the outlet aperture with the urethra orifice of the female during use.

Preferably, the centre of the radius of curvature of the pubic locating portion is located on the side of a radius of the vaginal locating portion remote from the one end of the axis.

By having the two portions tilted relatively to one another, a good leak free seal is provided at the body and reliable location is facilitated.

In a preferred embodiment, the central radius of the arc of curvature subtended by the vaginal locating portion is substantially vertical during use of the trumpet.

This again facilitates an appropriate location of the trumpet and a good seal.

In one case, the arc of curvature subtended by the vaginal locating portion is between 20° to 30°.

In another case, the arc of curvature subtended by the pubic locating portion is between 30° to 50°.

It is preferred that the outlet is located mostly within an arc of curvature subtended by the vaginal locating portion.

As a result, the outlet aperture is correctly aligned with the flow of urine from the female urethra orifice thereby avoiding splash-back and backing up of urine.

Conveniently, the surface of the bell extending from the outlet aperture along said axis towards said one end defines an angle of between 15° to 25° relative to a central radius of the arc of curvature subtended by the vaginal locating portion Preferably, the outlet aperture has an axis extending at an angle of between 125° to 145° relative to a central radius of the arc of curvature subtended by the vaginal locating portion.

This ensures correct alignment with the urine flow from the female urethra orifice.

Conveniently, the surface of the bell extending from the outlet along said axis towards said another end comprises a first section which is parallel to the axis of the outlet aperture and meets a second section defining an angle of between 5° to 20° relative to a central radius of the arc of curvature subtended by the vaginal locating portion.

It has been found that this form of surface presents a larger effective area at which the urine flow from the female urethra orifice may be directed without splash-back occurring since urine reflected therefrom still tends to pass into the outlet aperture.

According to another aspect of the present invention there is provided a urine sample collection apparatus having a urine funnelling trumpet as herein above defined.

The urine sample collection apparatus can have the forms mentioned above wherein the receptor is replaced by the urine funnelling trumpet as herein above defined.

According to another aspect of the present invention there is provided a waste urine collection apparatus having a urine funnelling trumpet as herein above defined.

Such an apparatus is of benefit to those who are disabled and/or bed-ridden, incontinent, and who may need to provide a urine sample in circumstances where assistance is not readily available. In such circumstances, there is merit in the availability of an apparatus into which they can urinate at will. The provision of such a facility is of great value, not only from the practical standpoint but also in the sense of improving the standard of life and general self-esteem of those unfortunate enough to be to any extent reliant on others for assistance in connection with the performance of their bodily functions.

According to another aspect of the present invention there is provided a leisure urination apparatus having a urine funnelling trumpet as herein above defined.

Thus, the need to use a receptor which must go under the outer labial lips is avoided.

Examples of the present invention will now be described with reference to the accompanying drawings, in which.

Figure 1:
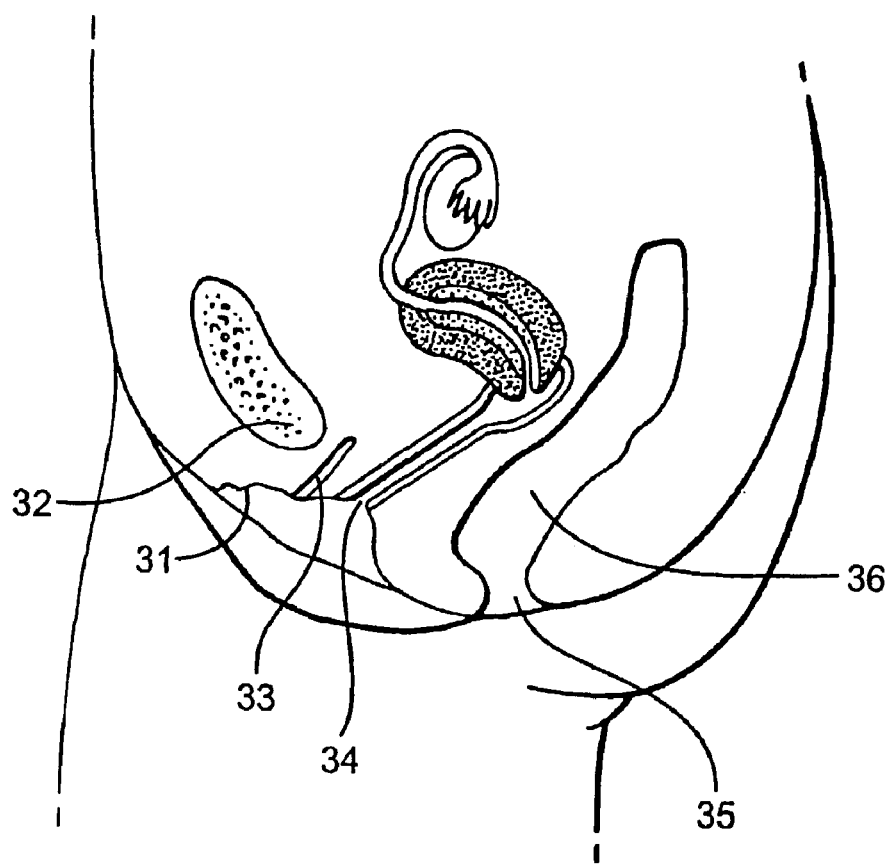
FIG. 1 illustrates a left side view of the female anatomy in the region of the urethra.

Components common to different figures bear common reference numerals.

As explained above, the present invention intends to provide a urination apparatus which can be an apparatus for unisex urine sample collection for testing of urine, for unisex waste urine collection for disposal of urine resulting from urination away from toilets, and for simplification of urination by women without sitting on a toilet, the latter being referred to hereinafter as a leisure urination apparatus. To be practical, such an apparatus must be small, compact, neat, and easily usable. However, a major problem which such an apparatus must overcome arises from the intrinsic differences in the emission characteristics of urine between male and female.

In the male, since the urethra is located at the end of the penis, which is manually movable to orient it in a desired direction, the emission direction of urine can to a reasonable degree be controlled. This enables urine to be directed into relatively small openings. Thus, a relatively small and compact apparatus can be produced which avoids splash-back, although there can still be a problem with urine backing up. Furthermore, urination can take place in a variety of different bodily postures.

In the female, the urethra is hidden by the labia. It is not commonly known, but an element of directional control can be obtained by careful manipulation of the region around the labia. In the absence of this, it has been found that during urination, the direction of emission varies over an angular range of up to 30°. Indeed, the direction can vary according to whether the female is seated or standing. Moreover, the direction varies from female to female according to a number of characteristics including, but not restricted to, age, weight and childbirth. Thus, the urination apparatus must take into account this variable angular range whilst ensuring that there is no splash-back of urine onto the body or backing up of urine onto the body.

Referring to FIG. 1, there is shown a left side view of the female anatomy. It can be seen that the female urethra orifice 33 is located between the clitoris 31 and the entrance to the vagina 34 and substantially below the pubis 32. The anus 35 and rectum 36 are also illustrated. It can be seen that the surface of the body in the proximity of the vulva generally curves from an upper or front portion in the region of the pubis to a lower or rear portion in the region of the anus. In fact, a plan view of this area (not shown) reveals that there is a concave curved strip, the radius of the curvature at the upper portion being quite similar to the radius of the curvature at the lower portion.

Figure 2:
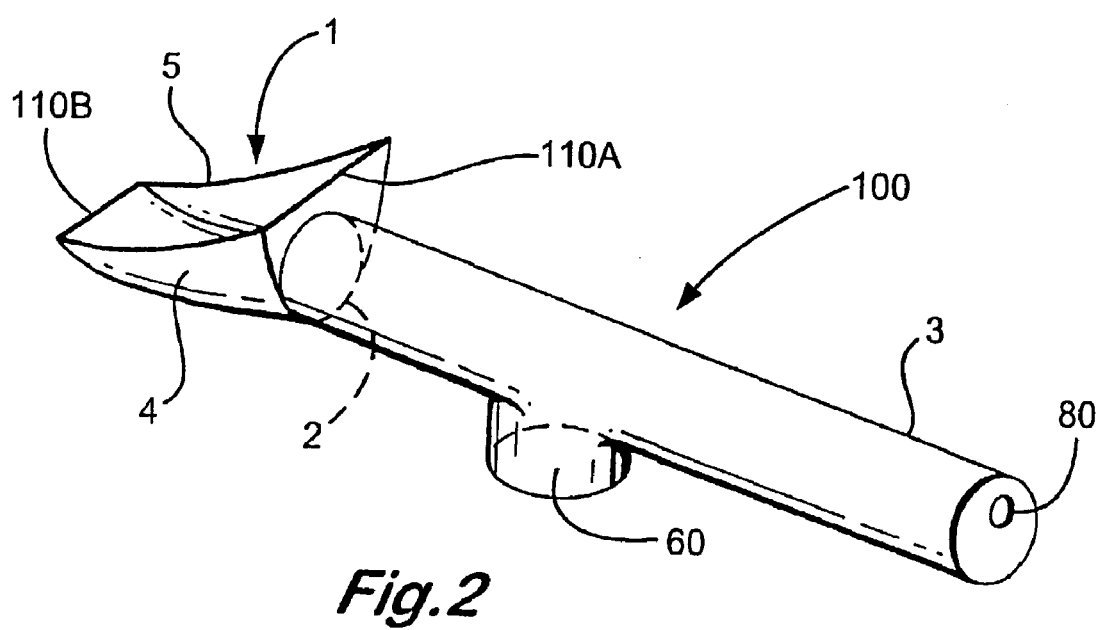
FIG. 2 illustrates an oblique perspective view of a first embodiment of a urine sample collection apparatus embodying the present invention.

FIG. 2 shows a first embodiment of a urine sample collection apparatus 100. The urine sample collection apparatus 100 comprises a urine receiving portion or receptor, generally identified by reference numeral 1, having an outlet aperture 2 coupled to one end of a generally elongate hollow tubular body or pipe portion 3 which extends therefrom. The receptor 1 is defined by a surface 4 which extends from the outlet aperture 2 to an oblong shaped rim 5, which defines a concave inlet surface area. The receptor thus has a resulting shape resembling a high sided shovel or a scoop.

The rim 5 is configured to fit intimately under the outer labial lips to cover the woman's urethra orifice 33 with one edge 110A of the rim directed towards the aforementioned upper portion and with the opposing edge 110B directed towards the aforementioned lower portion. This form of receptor is an internal receptor and typically has a dimension, extending from the edge 110A to 110B, in the region of 2.5 to 4 cm.

A sample container coupling 60 comprises a short hollow tube which is formed to open into the centre of the side of the tubular body corresponding to the edge 110B of the receptor. The sample container coupling 60 is located along the tubular body 3 to be spaced from the outlet aperture 2. The sample container coupling has an internal thread (not shown) onto which a standard urine sample collection container or bottle (not shown) can be screwed. The sample container coupling 60 is located such the sample container is orientated vertically downwards during use.

The end of the tubular body 3 remote from the outlet aperture 2 is closed apart from an excess outlet 80 in the form of a tear shaped aperture.

In use, a standard tubular urine sample collection container (not shown) is screwed into the threaded neck of the sample container coupling 60.

For a female, the receptor is located under the outer labial lips to cover the woman's urethra orifice with the edge 110A located higher than the edge 110B. This positioning may be achieved by covering the vagina area with the receptor 1 and then sliding it upwards into place over the urethra orifice before urinating.

In this position, the outer labia acts as a leak-proof fit and secures the internal receptor in place. By having such a leak proof fit and the location directly at the urethra orifice, the risk of contamination of the urine sample is reduced, and the risk of spillage and any associated drawbacks therefrom are reduced.

For a male, the tip of the penis is located against the receptor to cover the man's urethra orifice with the edge 110A located higher than the edge 110B before urinating.

The surface 4 of the receptor 1, the tubular body 3 and the location of the outlet aperture 2 are configured so as to encourage the free flow of urine into the apparatus 100. In this respect, it has been found that the outlet aperture 2 should be located so that in use it lies close to opposite the urethra opening 33. Thus, urine expelled from the urethra orifice under great pressure will tend to flow along the axis of the tubular body 3. With the receptor of this embodiment positioned as above, it is found that the outlet aperture 2 is aligned opposite the urethra orifice.

Thus, located, the sample container coupling 60 faces downward with the inlet surface of the sample container horizontal or facing towards the urine flow. The user then starts to urinate. The urine flows into the receptor 1, through the outlet aperture 2 and along the axis of the tubular body 3. As it passes the sample container coupling 60, a proportion of the urine falls under gravity into the collection container, with the air in the container being pushed out. The remainder of the urine flow continues down the tubular body 3 to pass through the excess outlet 80 into a toilet or urinal.

Once the collection container is full, the user can simply finish urinating because excess urine flows out of the excess outlet 80. Alternatively, the user can withdraw the apparatus 100 and continue to urinate, but this increases the likelihood of contamination to their hands.

Since the tubular body 3 is positioned in use substantially opposite the urethra orifice of a female in particular, so that the axis thereof is generally aligned with the natural flow axis of the urine from the body, the urine travels directly down the tubular body. As a result, the amount of splash-back onto the female body is insignificant and there is little if any backing up of urine along the tubular body and into the receptor.

After urination has been completed, the apparatus 100 is removed from the body. If the sample collection container is over full, the apparatus may be tipped slightly with the excess being poured through the excess outlet 80 while ensuring that sufficient urine is left in the collection container. The collection container is then unscrewed from the sample container coupling 60 and a secure closure (not shown) is screwed on. The apparatus 100 can then be disposed of or sterilised for further use.

With the apparatus of the present embodiment, it can be seen that a hygienic and simple urine sample collection apparatus is provided which does not suffer from the drawback of splash-back or backing up, particularly for the female user.

Figure 3:
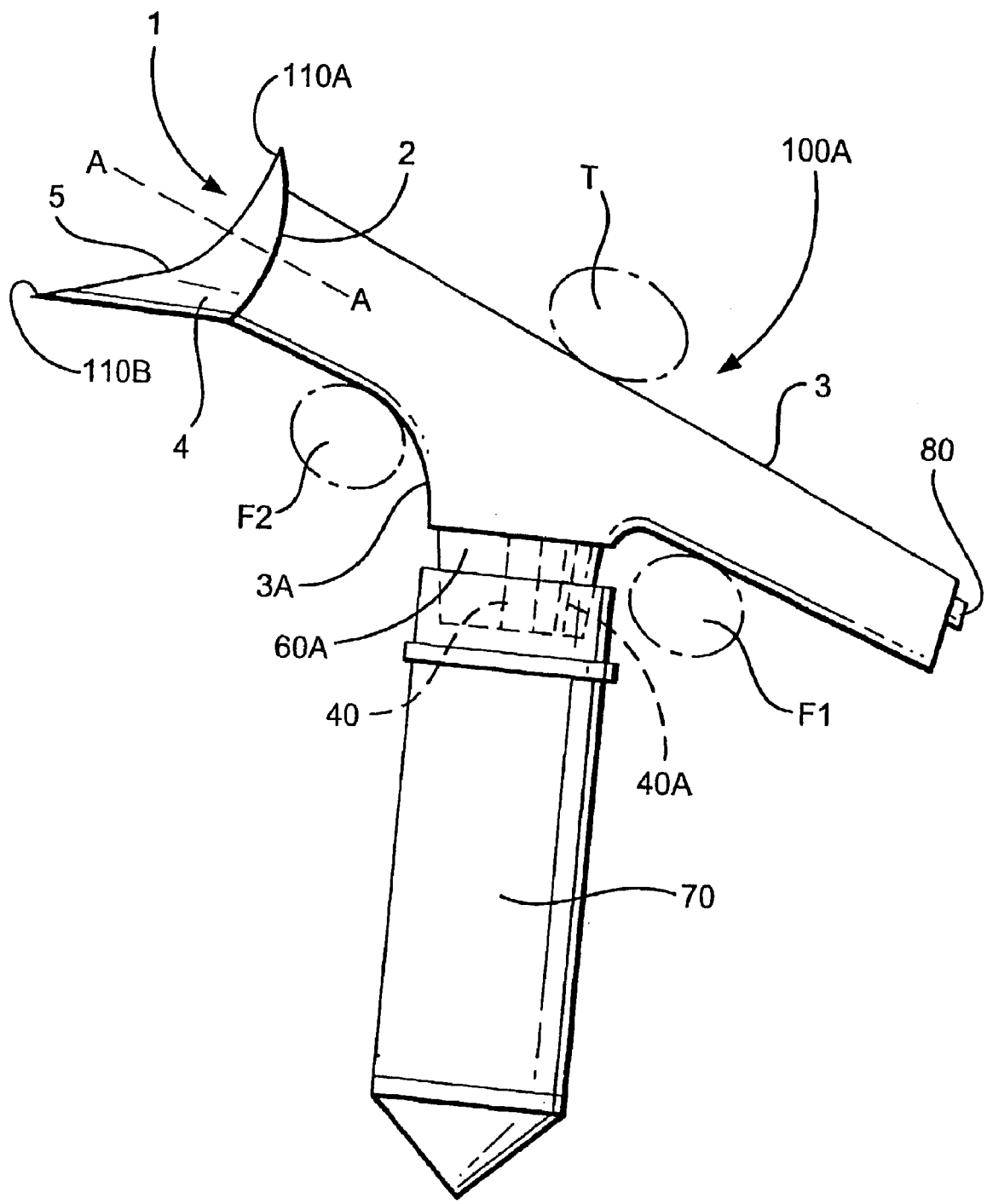
FIG. 3 illustrates a side view of a second embodiment of a urine sample collection apparatus embodying the present invention together with a standard tubular urine sample collection container attached.

FIG. 3 shows a second embodiment of a urine sample collection apparatus 100A together with a standard tubular urine sample collection container 70. The second embodiment is similar to that of FIG. 1 except that the sample container coupling 60A is formed as a short solid stub-like part having an exit passage 40 extending there through along with a smaller diameter vent pipe 40A, also extending there through for venting air during filling of the container 70. It will be apparent that the vent pipe 40A can be omitted in the event that air can adequately flow out of the exit passage 40 during filling with urine.

The external surface of the coupling tapers downwards in diameter with increasing distance from where it joins to the tubular body 3. The sample container coupling 60A is located along the tubular body 3 to be spaced from the outlet aperture 2 and is located such that it is orientated vertically downwards during use whereby the desired flow of urine through the exit passage 40 is assisted by gravity.

As with the embodiment of FIG. 2 and subsequent embodiments, the components of the apparatus 100A are formed without internal ribs or other components that could obstruct, or cause unwanted deviation of a flow of urine voided from a body at normal speeds and pressures. Moreover, the part of the tubular body 3 which joins the sample container coupling 60 on the side closer to the outlet aperture 2 (identified by reference numeral 3A) is curved, or alternatively angled, into the join in order to encourage the diversion of urine into the exit passage 40 from the flow of urine along the tubular body 3.

As with FIG. 2, the sample container coupling 60A is provided approximately in the centre of the lower surface of the tubular body 3, corresponding to the edge 110B, in order that there is a sufficient portion of the tubular body 3 provided at its end remote from the receptor 1 for the user to hold the apparatus comfortably. In addition, this spacing has been found to allow the urine to slow sufficiently to fall into the container 70 rather than flow past it. In this respect, as with FIG. 2, it is intended that the apparatus be held in a user's hand such that the user's fingers (F1, F2) are disposed beneath the tubular body 3 and splayed to either side of the sample container coupling. The apparatus is steadied by placing the thumb (T) on top of the tubular body 3 in a position roughly above the position of the sample container coupling. It has been found that the sample container coupling should preferably join the tubular body 3 at a distance of at least 1.5 cm from the aperture 2.

The use of the apparatus shown in FIG. 3 is similar to that of FIG. 2 except that the urine sample collection container 70 is attached to the sample container coupling 60A by means of a push fit or interference fit. Moreover, with the taper on the outlet coupling 60A, urine sample collection containers having necks of different diameters can be appropriately attached.

Figure 4:
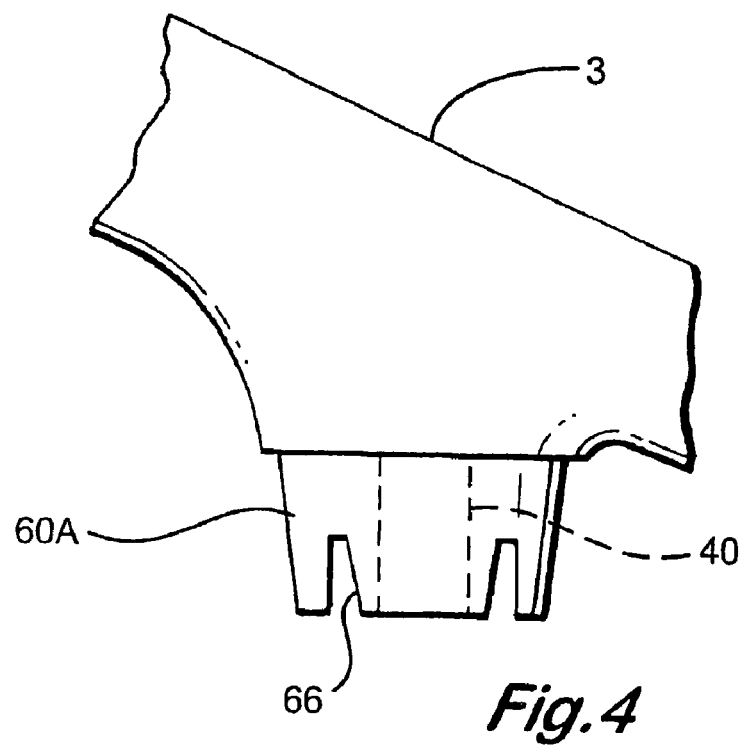
FIG. 4 illustrates an alternative form for the sample collection container coupling.

FIG. 4 illustrates a sample container coupling having an annular groove 66A formed in the lower surface (as illustrated), which groove extends into the body of the coupling with an increasing radius. In this way, smaller diameter urine sample collection containers can be pushed into the groove to provide an interference fit thereby increasing the number of different diameter containers that can be attached to the coupling.

In relation to FIG. 3, as with FIG. 2, it will be noted that when considering the axis of the tubular body 3, the edge 110A of the rim 5 is located closer to the outlet aperture 2 along that axis than the edge 110B of the rim 5 and that the sample container coupling 60 is located on the same side of the tubular body 3 that corresponds with the edge 110 B. The receptor 1 has this form since, during use by a female user, the outlet aperture 2 is located in the receptor 1 at a position which is slightly higher and which tends to locate the outlet aperture 2 more opposite the urethra orifice.

In addition, the rim 5 is formed such that when a female user is using the apparatus, the tubular body 3 extends at a particular angle from the body, that is the tubular body points in a generally downwards direction regardless of whether it is used in a standing or sitting position. In particular, the angle should be selected such that the axis of the tubular body is generally parallel with the direction of urine released during urination. In practice, this has been found to be in the region of 30° to 60° from horizontal when the rim 5 is located against the female body, and preferably 45°.

The sample container coupling may extend from the tubular body 3 with its axis at differing angles, for example FIG. 2 illustrates an angle of the order of 90°, whilst FIG. 3 illustrates an angle closer to 120°. The combination of angles of the tubular body 3 extending from the receptor and the sample container coupling 60 are selected whereby when the urine sample collection container is attached, the collection container is generally vertical or the plane of the upper edge of the collection container is horizontal or is angled to face towards the flow of urine during use of the apparatus.

Figure 6:
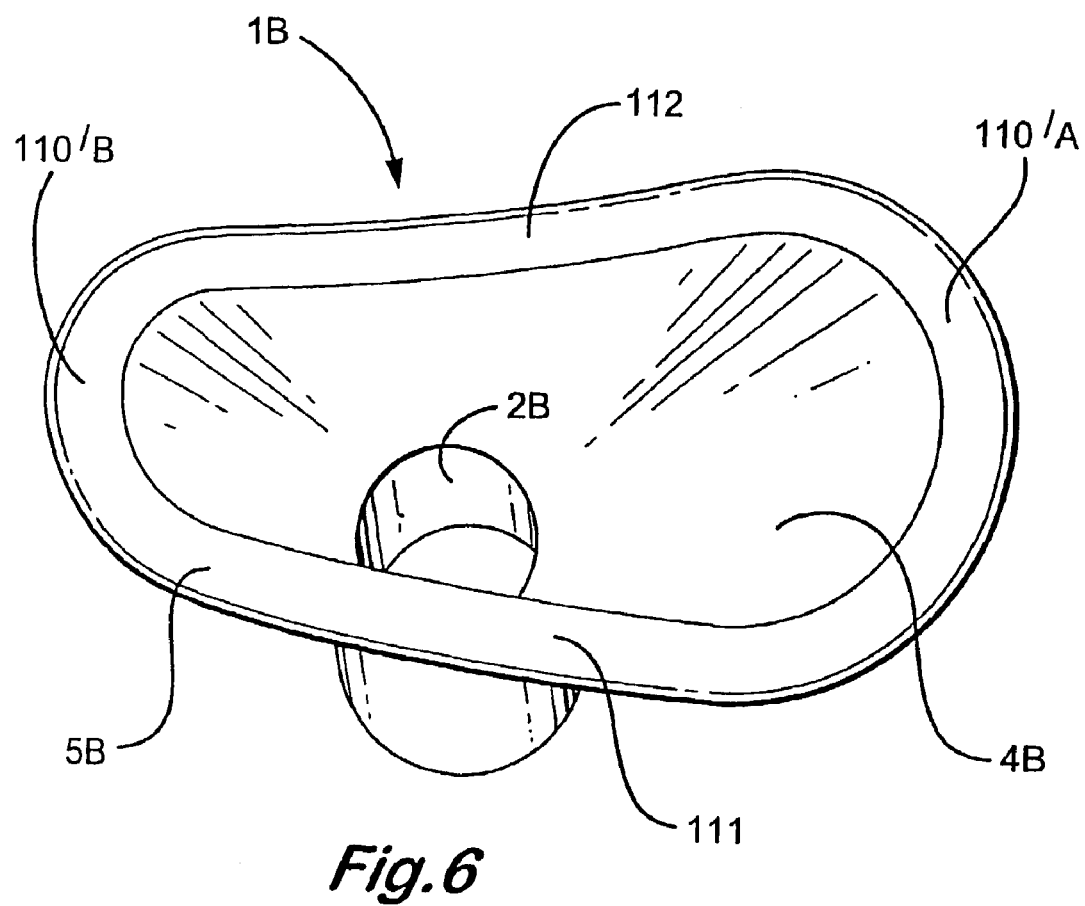
FIG. 6 illustrates a perspective view of the receptor forming part of embodiment shown in FIG. 5.
Figure 5:
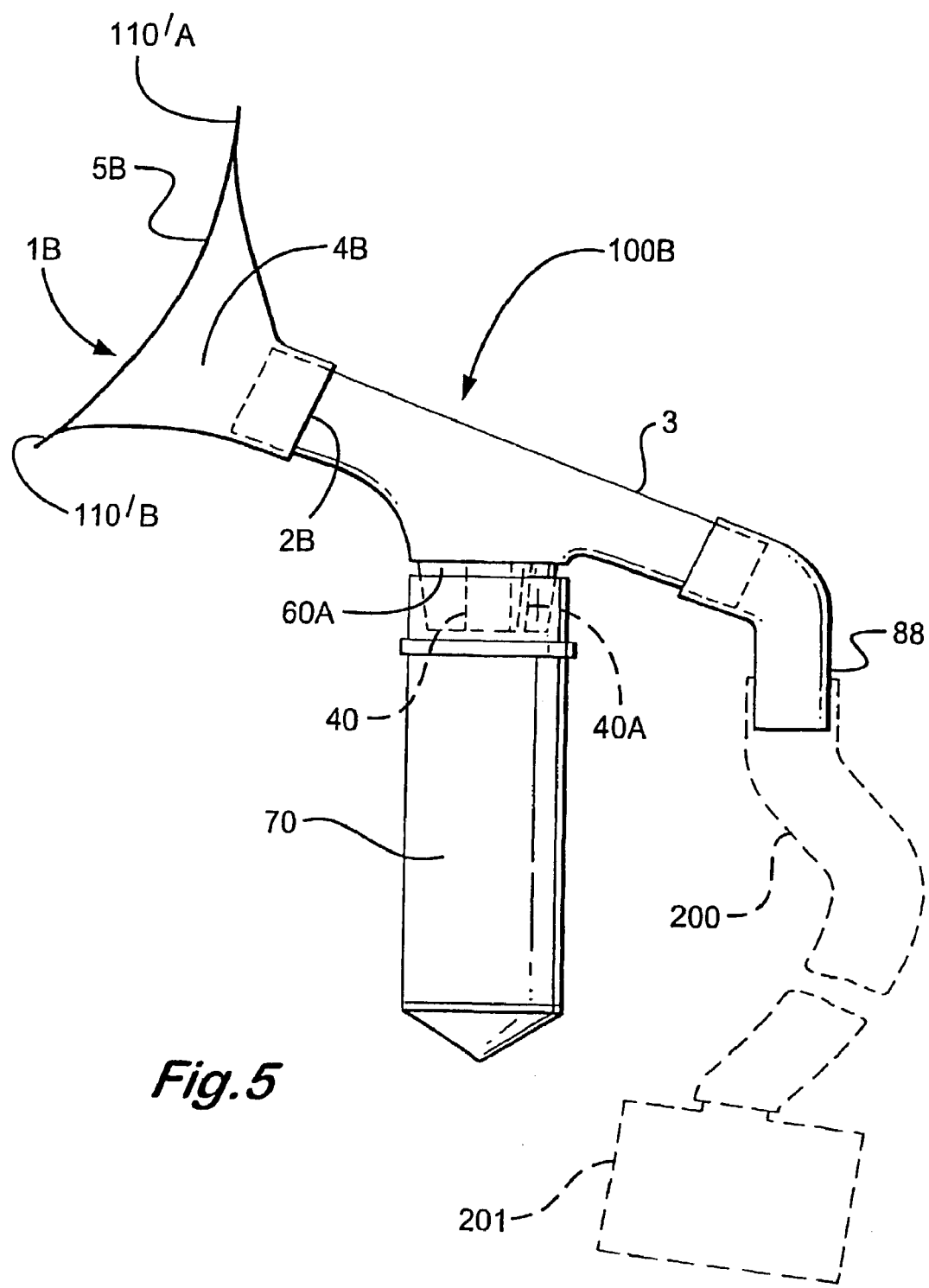
FIG. 5 illustrates a side view of a third embodiment of a urine sample collection apparatus embodying the present invention together with a standard tubular urine sample collection container attached, and a variation thereof to provide a waste urine collection apparatus.

Referring to FIGS. 5 and 6, there is shown a third embodiment of a urine sample collection apparatus 100B in which the receptor 1B, shown in greater detail in FIG. 6, is shaped to be placed over the outer labial lips, over the area of the vulva of a female, in order to generally cover the urethra orifice 33. This form of receptor is an external receptor. This form has general application for use by a wide range of the female population who may feel disinclined to use the internal receptor. The tubular body part of the apparatus 100B is similar to that shown in FIG. 3 apart from the end remote from the receptor.

Referring to FIGS. 5 and 6, it will be seen that, in this example, the receptor 1A comprises a surface 4B which extends from an outlet aperture 2B to a generally key-hole shaped body-contacting rim 5B comprising first and second arcuate portions, 110'A and 110'B, linked by substantially linear interconnecting portions 111 and 112. The rim 5B presents a smooth, slightly curved peripheral lip that is intended to be pressed into intimate contact with the female body to cover the outer labial lips.

The rim 5B defines an inlet surface for the receptor 1B which is slightly convex in shape and complementary to the curved strip of the female body between the upper and lower portions referred to above in relation to FIG. 1. For comfort and soundness of fit, the rim 5B is shaped with a general configuration being that the arcuate portions 110'A and 110'B are disposed somewhat further from the outlet aperture 2B along the axis of the tubular body 3 than the centre of the interconnecting portions 111 and 112.

The receptor 100B is shaped and configured for use with the arcuate portion 110'A disposed towards the upper portion of a female user and the arcuate portion 110'B disposed towards the lower portion of a female user. Whilst a female user is aware of the location of their anus, they are typically not so clearly aware of the location of the urethra orifice. Since the apparatus 100B is intended to take a urine sample, it has been found that the female user using the receptor 1B will not locate it over the vulva region such that the arcuate portion 110'B is located over the anus. For this reason, the anus provides a reference point for location of the receptor 1B. On this basis, the outlet aperture 2, as defined by the surface 4B, can be positioned such that during use, for a typical range of female users, the outlet aperture 2 is located as close as possible to being opposite the urethra orifice.

The dimension of the receptor 1B in this embodiment comprises a length of 6.5 cm and a maximum width of 3.2 cm and a minimum width of 2.0 cm. The rim 58 has a radius in the region of 10 cm whilst the tubular body 3 has an overall length of 9 cm. The diameter of the exit aperture 40 in the sample container coupling 60A is 0.8 cm and is located centrally along the tubular body 3.

The surface 4B is shaped to define a bowl-like concavity communicating with the outlet aperture 2 which links directly to the tubular body 3. This shape has been found to reduce splash-back during use by a female and substantially avoids backing up of urine in the tubular body.

In the present embodiment, the receptor 1B is a separate component which is a push-fit to the tubular body 3. In addition, an excess aperture is not provided. Instead, a curved outlet or diverting tube 88 is pushed over the end of the tubular body 3 to direct urine flow in the body downwards. The diverting tube may be detachable or integral with the tubular body. Of course, the diverting tube may be omitted and the tubular body can instead include the excess aperture 80.

The apparatus 110B is used in the same manner as the apparatus of FIGS. 2 and 3 except that the receptor 1B is located over the outer labial lips.

The apparatus described above concerns a urine sample collection apparatus. This apparatus can be changed to a unisex waste urine collection apparatus for disposal of urine resulting from urination away from toilets. In essence, the tubular body is formed without the sample container coupling and hence comprises a simple tubular body connecting at one end to the outlet aperture 2. Then, a flexible elongate pipe 200, shown by dotted lines in FIG. 5, is attached to the end of the tubular body 3 remote from the outlet aperture 2, in this case the diverting tube 80. The other end of the flexible pipe 200 is connected to an expandable bag 201. The bag thus forms a waste container, although it could be replaced by a bottle.

Thus, when a user needs to urinate, they locate the receptor in the appropriate position, as mentioned above for providing a sample, and urinate. The urine will then flow down the tubular body 3, down the pipe 200 and into the bag 201. Consequently, a simple and easy apparatus is provided for collection of urine resulting from urination away from a toilet or urinal.

In a similar manner, by not including the pipe 200, an apparatus is provide for simplification of urination by women without sitting on a toilet. In this respect, when a female needs to urinate, they locate the receptor in the appropriate position, as mentioned above for providing a sample, and urinate. Since the tubular body 3 provides a means for directional control of the urine flow, the user can direct the urine to a desired location. Moreover, since urination using the receptor described above can take place in a standing position, a female user can use such an apparatus standing up directing the urine into a urinal or into a conventional toilet without sitting down. Indeed, such an apparatus can be used in the open with the advantage that there is a much reduced exposure of the female body during standing usage compared with conventional urination by squatting.

In arriving at the embodiments described above, that is a urination apparatus which can be an apparatus for unisex urine sample collection for testing of urine, for unisex waste urine collection for disposal of urine resulting from urination away from toilets, and for simplification of urination by women without sitting on a toilet, it was found with the prior art that if the flow of urine by a female during urination is rapid, back-splashing and backing up of urine can take place. It is believed that a primary cause of this results from the outlet aperture 2 not being located directly opposite the urethra orifice so that urine flowing therefrom will not preferentially flow down the tubular body 3. Moreover, for females usage, it has been found that correctly positioning the outlet aperture within the receptor to overcome this problem is very difficult due to variation in the female anatomy and partly due to variation in positioning of the receptor in use.

Figure 7:
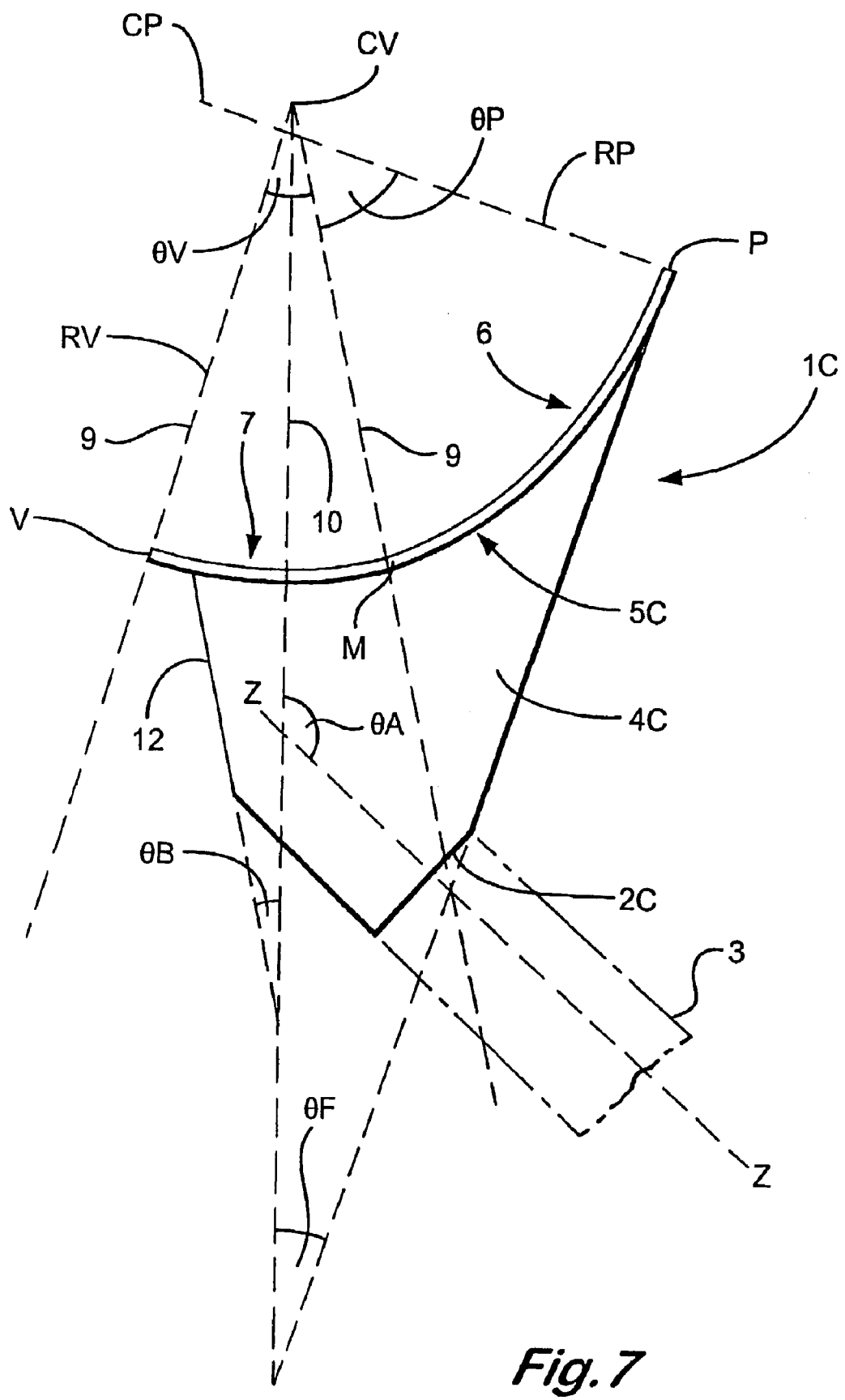
FIG. 7 illustrates a side view of a urine funnelling trumpet embodying the present invention.
Figure 8:
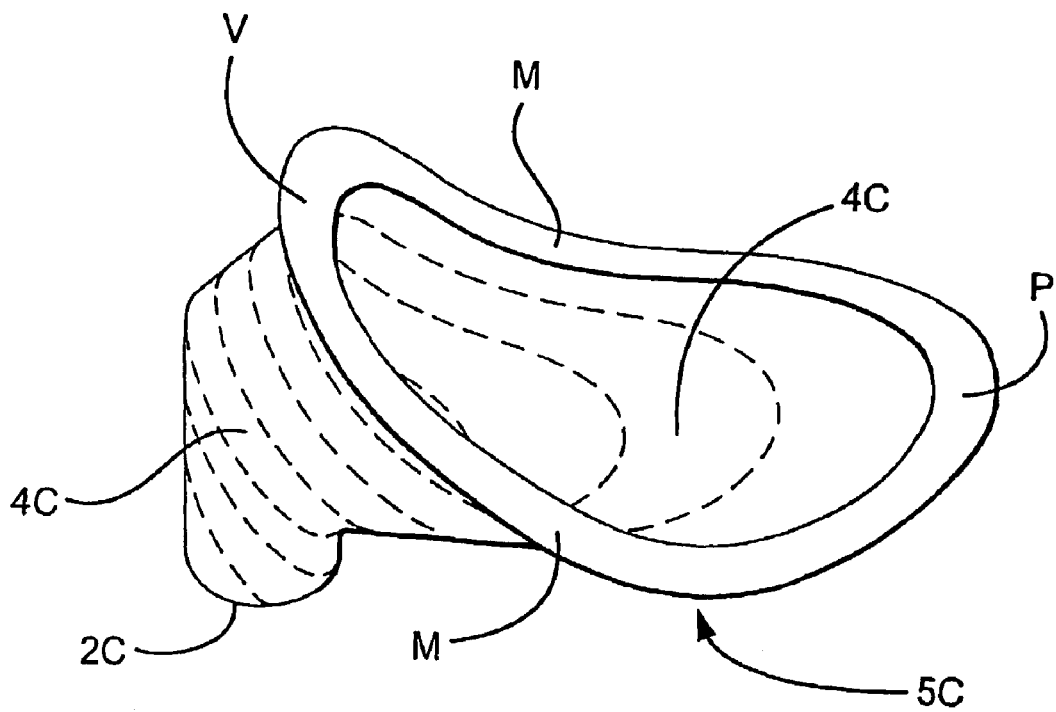
FIG. 8 illustrates an oblique perspective view of the urine funnelling trumpet shown in FIG. 7.
Figure 9:
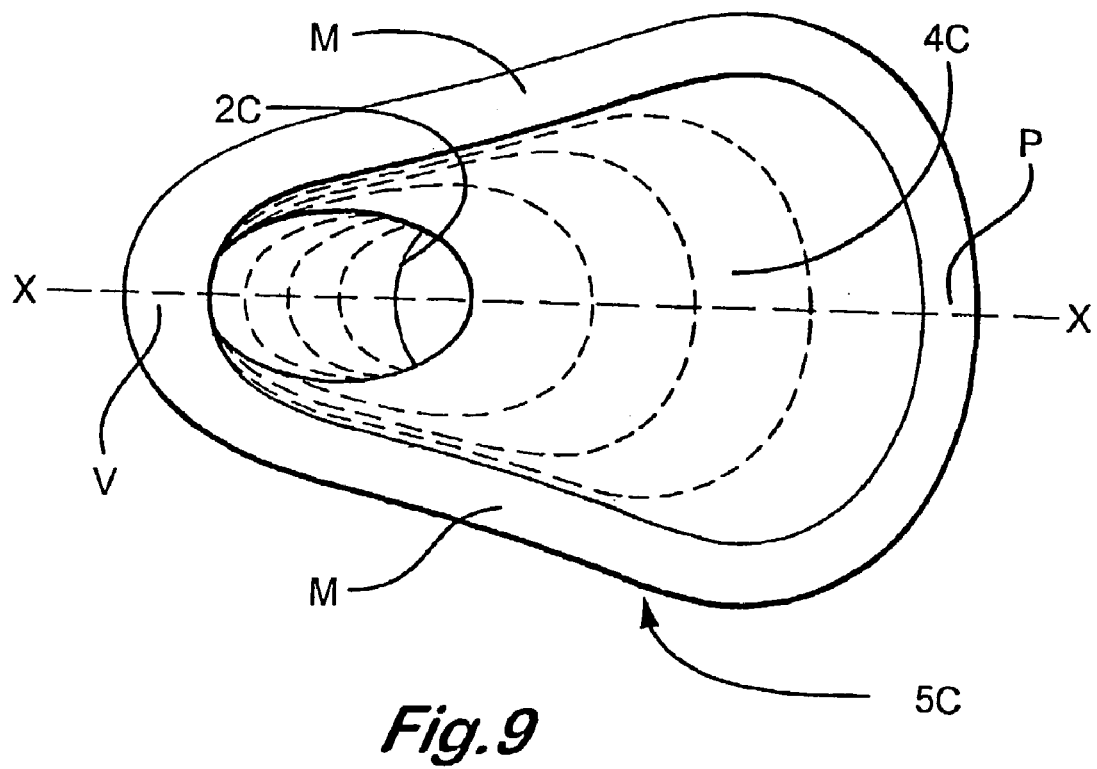
FIG. 9 illustrates a top plan view of the urine funnelling trumpet shown in FIG. 7.

Whilst the above embodiments reduce the problems, FIGS. 7, 8 and 9 illustrate a receptor or trumpet which substantially entirely overcomes these problems. These figures show a receptor 1C which it is believed positions the outlet aperture correctly and enables reliable positioning of the receptor by females during use. In these figures the receptor is defined as a urine funnelling trumpet 1C comprises an outlet aperture 2C defining a generally planar circular cross section. The outlet aperture has an axis Z-Z which extends perpendicularly from the cross section thereof to join and be aligned with the axis of an elongate tubular body 3 (shown in shadow outline) forming part of a urination apparatus in the form of a urine sample collection apparatus, a waste urine disposal apparatus, or a leisure urination apparatus.

From the edge of the aperture a surface 4C flares out and extends to a rim 5C to form a bell. It will be appreciated that the precise shape of the bell will vary according to the form of the surface 4C as will be apparent hereinafter. The rim defines an inlet surface for the urine funnelling trumpet. The rim is intended to be pushed lightly onto the body of a female user.

As can be seen from FIG. 9, the inlet area defined by the rim 5C has a long axis X extending between end points P (pubic) and V (vaginal). Points M are located between the points P and V on the rim 5C.

The part of the rim between the point P and the points M defines a pubic locating portion 6 which has a radius of curvature RP as measured from the point P to a point CP.

The part of the rim between the point V and the points M defines a vaginal locating portion 7 which has a radius of curvature RV as measured from the point V to a point CV.

Taken along the axis X, the pubic locating portion 6 subtends an arc having an angle θP whilst the vaginal locating portion 7 subtends an arc having an angle θV.

The urine funnelling trumpet 1C has been produced so that when positioned by females for use, the line 10 (as illustrated) should be aligned with the centre line of the body, that is to say substantially vertical. In this position, the line 10 substantially bisects the arc having an angle θV, that is to say the point CV lies on line 10.

It will be seen that as the arc of the angle θV is extended beyond the vaginal locating portion 7, as shown by the dotted lines 9, the aperture 2C mostly lies within this arc. Moreover, the axis Z-Z makes an angle of θA with the line 10.

It will be seen that the surface 4C of the bell extending along the axis X-X from the outlet aperture 2C to the point P makes an angle of θF with the line 10.

It will be seen that the surface 4C of the bell extending along the axis X-X from the outlet aperture to the point V comprises a first section 11, parallel to the axis Z-Z, which meets a second section 12 extending down from the point V making an angle of θB with the line 10.

Table 1 shows the angles that are used in the preferred embodiment of the invention illustrated, along with the ranges that can be used.

TABLE 1

| Value | Illustrated | Range |
| --- | --- | --- |
| θA | 135° | 125°-145° |
| θB | 10° | 5°-20° |
| θF | 20° | 15°-25° |
| θP | 60° | 45°-75° |
| θV | 25° | 20°-30° |

In the illustrated embodiment, the value of RV is 70 mm and that of RP is 75 mm. In addition, the points CV and CP are separated by a distance of 15 mm, this distance being on the vaginal side of and substantially perpendicular to the line 10. It will be appreciated that these values can be changed. Preferably, the value of RV is not more than 20% less than RP. The inclination between the vaginal locating portion and the pubic locating portion is obtained by having the distance between the points CV and CP. The diameter of the outlet aperture 2 is 21 mm and preferably between 15 mm and 25 mm.

The urine funnelling trumpet of the present invention can be integrally formed with or attached to a tubular extension, such as that shown by reference numeral 3 in the earlier described figures. This tubular extension can then take a form as described above to obtain a urine sample collection apparatus, a waste urine collection apparatus, or a leisure urination apparatus.

In use, the rim 5C is located against a female body with the pubic locating portion located over the pubic bone and the vaginal locating portion located over the vaginal lips. The user then urinates and the apparatus is used as described above.

It has been found that the inclination of the pubic locating portion towards the vaginal locating portion matches the anatomy of females well. By dimensioning the vaginal locating portion to cover the vaginal lips, it has been found that leakage during urination does not occur. Indeed, due to the angles selected and the fact that the surface 4C of the bell in the region of the point P meets that point substantiality at a tangent to the arc formed by angle θP, it has been found that a generally flattened area is produced in the region of the point P. This has been found to encourage females to identify this part with their pubic area thereby automatically providing a clue to the orientation and positioning of the trumpet. Furthermore, due to the flattened area, a good seal is provided at this point even with variations in the anatomy of the female.

In addition, by having the particular angles mentioned above and the outlet 2C mostly within the arc subtended by the angle θV, splash back and backing up of urine in the trumpet does not occur. The urine funnelling trumpet of the present invention has been tested by females in a standing, sitting and prone position with differing types of urine sample collection apparatus, waste urine collection apparatus, and leisure urination apparatus as described above. It has been found that the females users do not suffer from any splash back. Indeed, they have are no more wetness than that resulting from urination without the trumpet. Moreover, no leakage around the rim 5C has occurred during the relatively high pressure conditions that exist during urination. In addition, backing up of urine in the bell has not been observed if the tubular body 3 and subsequent parts of the apparatus provide sufficient drainage away from the bell 4.

Thus, the urine funnelling trumpet enables reliable location of the trumpet when used by females and this together with the correct location of the outlet aperture 2C provides a receptor which substantially avoids splash-back and backing up problems.

Although the embodiment of FIGS. 7 to 9 has been described as for use with a urine sample collection apparatus, a waste urine collection apparatus and a leisure urination apparatus, it will be apparent that it can comprise an integral part or a major component of all of such apparatus. In fact, it can also be used as part of a kit for female incontinence. Moreover, whilst the urine funnelling trumpet has particular usage for females, it can still be used by males.

It will be apparent that the embodiments described above show one example only of the relative angular disposition and location of the outlet aperture, the tubular body and the sample container coupling. In particular, the orientation of the sample container coupling may be oriented to the tubular body at an angle significantly different from 90°. Moreover, the exit passage in the coupling can be angled to the axis of the coupling rather than parallel thereto.

The excess aperture described above was tear-shaped or pear-shaped such that, during use of the apparatus, the narrower end of the excess aperture is located lower in the end wall of the tubular body 3 than is its wider end. Whatever form is taken by the excess aperture 8, there can be an advantage in the formation of an associated lip, external of the end of the tubular body 3 onto which a flexible sac, length of tubing, or diverting tube may be attached by means of a resilient or push fit neck so that excess urine can flow out of the excess aperture 8 without spillage into the sac or tubing as the case may be.

The sample container coupling may be pivotally mounted with respect to the tubular body 3 so that the angle of the sample container with respect of the urine sample collection apparatus can be altered to an angle which is comfortable for the user while ensuring that the sample container is adequately filled. This pivotal motion may be achieved by connecting the coupling to the tubular body with a thinned portion of material, by using a material that is naturally malleable or otherwise constructed or formed to be so or by using a tubular outlet of corrugated, concertina-like construction that can accommodate relative movement between adjacent folds.

The receptors described above provide greater comfort and security in use, and also reduce the risk of leakage at the body due to a vacuum effect produced during urine flow through the apparatus and also because any splashing back of the urine only affects a small area. In addition, for a female user, a woman can locate the receptor without having to take down her trousers or panties. In this connection, trousers can be unzipped or unbuttoned and panties moved to one side before locating the receptor. Then, without having to sit on a toilet seat, the woman can urinate with confidence into the apparatus.

The present invention enables the use of the apparatus by a female in a sitting or standing position. Since the woman may use the apparatus standing up, the apparatus can also aid women who have difficulty hovering over public toilet seats, for example the permanently or temporarily disabled. Moreover, urine is sterile and thus urinals have much less bacteria than toilets which have had feces in. It has been found that women who urinate over or on such a toilet have a higher risk of aerosol contamination of the vulva area than a man or women using a urinal.

It will be apparent that the apparatus and trumpet described above can be produced from plastics material (either hard or soft such as EVA), rubber, papier mâché or metal, depending upon factors such as cost and the need for sterilisation and re-usability.

The apparatus can be formed as a single integral unit or may be a separate tubular body part connectable by suitable means to a receptor.

It will be appreciated that the sample container coupling can be arranged to connect to a urine sample collection container in many different ways, including, but not restricted to bayonet fitting, screw fitting, or push-fit fitting. Moreover, whilst a coupling for circular cross section sample collection containers has been illustrated, the present invention is not limited to such containers.

It will be understood that the embodiment illustrated shows one application of the invention only for the purposes of illustration. In practice the invention may be applied to many different configurations, the detailed embodiments being straightforward for those skilled in the art to implement.

The invention claimed is:

1. A urine funnelling trumpet comprising:
a relatively narrow outlet aperture flaring out to a bell with a rim defining a perimeter of a urine inlet area;
wherein the inlet area has a long axis with a pubic locating portion extending from one end of the axis to meet a vaginal locating portion extending from the other end of the axis, the inlet area having a substantially symmetrical curvature about said axis;
wherein the inlet area of the vaginal locating portion has a vaginal locating curvature along said axis and the inlet area of the pubic locating portion has a pubic locating curvature along said axis which is tilted to be inclined relatively towards the vaginal locating curvature;
wherein the side of the bell flaring out from the outlet aperture meets the pubic locating portion at the rim substantially as a tangent to the pubic locating curvature to provide a generally curved surface in that region, the intersection of said curved surface with a vertical plane passing through said long axis defining a straight line.

2. A urine funnelling trumpet according to claim 1 wherein the vaginal locating portion is dimensioned to fit substantially closely around the vaginal lips of a female user.

3. A urine funnelling trumpet according to claim 1 wherein the curvature of the vaginal locating portion along said axis has a constant radius which is no more than 20% smaller than the constant radius of the curvature of the pubic locating portion along said axis.

4. A urine funnelling trumpet according to claim 3 wherein the point from which the radius of curvature of the pubic locating portion along said axis extends is located remote from the one end of the axis relative to one side of the point from which the radius of curvature of the vaginal locating portion along said axis extends.

5. A urine funnelling trumpet according to claim 1 wherein a line between the point from which the radius of curvature of the vaginal locating portion along said axis extends and the center of the arc of curvature subtended by the vaginal locating portion is substantially vertical during use of the trumpet.

6. A urine funnelling trumpet according to claim 1 wherein the arc of curvature subtended by the vaginal locating portion is between 20° to 30°.

7. A urine funnelling trumpet according to claim 1 wherein the arc of curvature subtended by the pubic locating portion is between 30° to 50°.

8. A urine funnelling trumpet according to claim 1 wherein the surface of the bell extending from the outlet along said axis towards said one end defines an angle of between 15° to 25° relative to a radius which is central to the arc of curvature subtended by the vaginal locating portion.

9. A urine funnelling trumpet according to claim 1 wherein the surface of the bell extending from the outlet along said axis towards said another end comprises a first section which is parallel to the axis of the outlet aperture and meets a second section defining an angle of between 5° to 20° relative to a radius which is central to the arc of curvature subtended by the vaginal locating portion.

10. A urine sample collection apparatus having a urine funnelling trumpet according to claim 1.

11. A urine sample collection apparatus according to claim 10 having the outlet aperture connected to a generally elongate tubular portion having an outlet in the side thereof including a coupling formed for releasably mounting an open topped urine sample collection container thereto in a direction extending generally away from the axis of said tubular portion.

12. A waste urine collection apparatus having a urine funnelling trumpet according to claim 1.

13. A leisure urination apparatus having a urine funnelling trumpet according to claim 1.

14. A urine sample collection apparatus comprising:
a generally elongate tubular portion having an outlet in the side thereof including a coupling formed for releasably mounting an open topped urine sample collection container thereto in a direction extending at a fixed angle other than a right angle from the axis of said tubular portion; and
a receptor for reception of urine, the receptor having a surface portion extending from a rim, which bounds a generally concave shaped inlet surface, to an aperture from which said tubular portion extends in a direction generally away from said inlet surface;
wherein the edge of the rim on the side corresponding to said outlet is displaced along the axis of the tubular portion further from said aperture than the opposing edge of said rim.

\* \* \* \* \*